United States Patent [19]

Dege et al.

[11] 4,311,822

[45] Jan. 19, 1982

[54] INTERFACIAL PRODUCTION OF POLY(ESTER CARBONATE) OR POLYESTER INCLUDING ACID CHLORIDE SYNTHESIS

[75] Inventors: Gerald J. Dege, Flanders; Leon Segal, Randolph; Bruce T. DeBona, Madison; Robert S. Cooke, Morris Plains, all of N.J.

[73] Assignee: Allied Corporation, Morristown, N.J.

[21] Appl. No.: 145,901

[22] Filed: May 2, 1980

[51] Int. Cl.$^3$ .............................................. C08G 63/62
[52] U.S. Cl. ................................... 528/176; 528/182; 528/190; 528/191
[58] Field of Search ................ 528/176, 182, 190, 191

[56] References Cited

U.S. PATENT DOCUMENTS

| | | | |
|---|---|---|---|
| T886,004 | 5/1971 | Atadan | 260/525 |
| 3,629,328 | 12/1971 | Stautzenberger et al. | 260/525 |
| 3,637,841 | 1/1972 | Martin | 260/544 M |
| 3,776,886 | 12/1973 | Schreyer | 260/544 L |
| 3,869,485 | 3/1975 | DeLong | 260/408 |
| 3,875,226 | 4/1975 | Doorenbos et al. | 260/544 L |
| 3,878,244 | 4/1975 | Zengel et al. | 260/544 M |
| 3,888,921 | 6/1975 | Yamamoto et al. | 260/525 |
| 4,129,594 | 12/1978 | Baker et al. | 260/544 D |
| 4,156,069 | 5/1979 | Prevonsek et al. | 528/182 |
| 4,173,708 | 11/1979 | Palmen et al. | 562/460 |
| 4,194,038 | 3/1980 | Baker et al. | 528/182 |
| 4,255,556 | 3/1981 | Segal et al. | 528/190 |

OTHER PUBLICATIONS

Wagner et al., *Synthetic Organic Chemistry,* John Wiley & Sons, NY, 1953, pp. 546-557.

*Primary Examiner*—Maurice J. Welsh
*Attorney, Agent, or Firm*—Alan M. Doernberg; Gerhard H. Fuchs

[57] ABSTRACT

A process for producing poly(ester carbonates) and polyesters by reacting an aromatic or cycloaliphatic dicarboxylate salt such as sodium terephthalate with phosgene in an organic solvent in the presence of a catalytic amount of a tertiary nitrogen compound such as pyridine, optionally separating the suspended by-product inorganic salt and then interfacially reacting with a bisphenol such as bisphenol A. Excess phosgene in the diacid chloride synthesis can be carried over to the polymerization if a poly(ester carbonate) is to be produced or removed if a polyester is to be produced. Certain low levels of a tertiary nitrogen compound with a pyridine nucleus in the organic solution do not interfere with the interfacial polymerization.

20 Claims, No Drawings

INTERFACIAL PRODUCTION OF POLY(ESTER CARBONATE) OR POLYESTER INCLUDING ACID CHLORIDE SYNTHESIS

BACKGROUND OF THE INVENTION

The production of a poly(ester carbonate) from monomers such as bisphenol A, terephthaloyl chloride and phosgene is described in U.S. Pat. Nos. 4,156,069 of Prevorsek et al. and 4,194,038 of Baker et al. In U.S. Pat. Nos. 4,194,038 and 4,129,594, the terephthaloyl chloride, or similar acid chloride, is synthesized from the corresponding aromatic or cycloaliphatic acid by reaction with phosgene in organic solution. Thereafter, in U.S. Pat. No. 4,194,038, phosgene and a dihydric aromatic alcohol such as bisphenol A are added in a prescribed manner to the solution to produce the poly(ester carbonate). Accordingly, the process of U.S. Pat. No. 4,194,038 provides for the production of the poly(ester carbonate) from the aromatic or cycloaliphatic dicarboxylic acid without isolation or the acid chloride by solution processes in a single reaction chamber.

For various reasons, it is often desirable commercially to produce condensation polymers such as polyesters and poly(ester carbonates) by an interfacial process in which the bisphenol is introduced as an aqueous solution of the corresponding alkali metal salt. Such an interfacial process is described in copending, commonly assigned U.S. Pat. application Ser. No. 29,422 of Segal et al., field Apr. 12, 1979 now U.S. Pat. No. 4,255,556 (1981), proceeding from the acid chloride such as terephthaloyl chloride as the reactant. Terephthaloyl chloride is introduced in relatively pure form, and no consideration is given in the disclosure of this copending application to complications due to the presence of catalysts or by-products from the production of the acid chloride. It would be desirable to produce poly(ester carbonates) by an interfacial process in a single reaction chamber or, at least, to produce same from the aromatic or cycloaliphatic acid chloride without isolation or extensive purification of the acid chloride from catalysts or by-products of its synthesis.

BRIEF DESCRIPTION OF THE INVENTION

It has been discovered that aromatic and cycloaliphatic acid chlorides can be used in an interfacial polymerization without isolation or extensive purification only if any tertiary nitrogen compound with a pyridine nucleus present in the acid chloride is reduced below a critical level. It has also been discovered that such aromatic and cycloaliphatic acid chlorides can be used directly in interfacial polymerizations without isolation or extensive purification only by substantial modification of the method by which they are produced from the corresponding acid and phosgene compared to the previously disclosed method of U.S. Pat. No. 4,129,594. While the synthesis of the aromatic or cycloaliphatic carboxylic acid chloride by the different method is the subject of an application of Robert S. Cooke and Bruce Van Buskirk Ser. No. 146,942, filed May 2, 1980 commonly assigned and filed herewith, the process in which such synthesis in certain forms (with a particular range of levels of tertiary nitrogen compound) is combined with an interfacial polymerization to form a poly(ester carbonate) is included in the subject matter of the present application.

Accordingly, the present invention includes a process for the production of a poly(ester carbonate) which comprises:

(a) reacting an alkali metal or alkaline earth metal salt of an aromatic or cycloaliphatic dicarboxylic acid in an inert organic solvent with phosgene in the presence of at least one tertiary nitrogen compound to form a corresponding aromatic or cycloaliphatic dicarboxylic acid chloride dissolved in the organic solvent, carbon dioxide and an alkali metal or alkaline earth metal chloride salt suspended in the organic solution;

(b) preferably, but not necessarily, separating the suspended alkali metal or alkaline earth metal chloride from the organic solution; and (c) mixing the organic solution with an aqueous solution of an alkali metal or alkaline earth metal salt of a bisphenol under sufficient agitation and with sufficient phosgene and tertiary nitrogen polymerization catalyst present to form a poly(ester carbonate) polymer.

The present invention also includes a process for interfacially producing a poly(ester carbonate) which comprises:

(a) mixing an organic solution of an inert organic solvent containing an aromatic or cycloaliphatic dicarboxylic acid halide and a tertiary nitrogen compound containing a pyridine nucleus in an amount between about 0.1 and about 10% by moles of carboxylic acid halide with an aqueous solution of an alkali metal salt of an aromatic dihydric alcohol in the presence of a catalytic amount of a tertiary amine polymerization catalyst, with phosgene also being present, to form a poly(ester carbonate) with carbonate moieties and moieties derived from the aromatic or cycloaliphatic dicarboxylic acid halide and from the bisphenol, (b) separating aqueous and organic phases after the poly(ester carbonate) is formed, (c) washing the organic phase substantially free of halide, and (d) recovering the poly(ester carbonate) from the washed organic phase.

The present invention also includes a process for the production of a polyester which comprises:

(a) reacting an alkali metal or alkaline earth metal salt of an aromatic or cycloaliphatic dicarboxylic acid in an inert organic solvent with phosgene in the presence of at least one tertiary nitrogen compound to form a corresponding aromatic or cycloaliphatic dicarboxylic acid chloride dissolved in the organic solvent, carbon dioxide and an alkali metal or alkaline earth metal chloride salt suspended in the organic solution;

(b) preferably, but not necessarily, separating the suspended alkali metal or alkaline earth metal chloride from the organic solution; and (c) removing any unreacted phosgene from the organic solution; and (d) mixing the organic solution with an aqueous solution of an alkali metal or alkaline earth metal salt of a bisphenol under sufficient agitation and with sufficient tertiary nitrogen polymerization catalyst present to form a polyester polymer.

DETAILED DESCRIPTION OF THE INVENTION

The present invention involves, in at least one form, the use of the acid chloride synthesis process described and claimed in the copending application of Cooke and Van Buskirk. That method involves the reaction of an alkali metal or alkaline earth metal salt of an aromatic or cycloaliphatic dicarboxylic acid with phosgene in an inert organic solvent in the presence of a tertiary nitrogen compound preferably containing a pyridine nucleus to form the corresponding aromatic or cycloaliphatic dicarboxylic acid chloride. Suitable aromatic dicarboxylic acids include substituted and unsubstituted forms of isophthalic and terephthalic acid, naphthalene dicarboxylic acid, benzophenone dicarboxylic acid, anthracene dicarboxylic acid and similar acids represented generally by the following formulae:

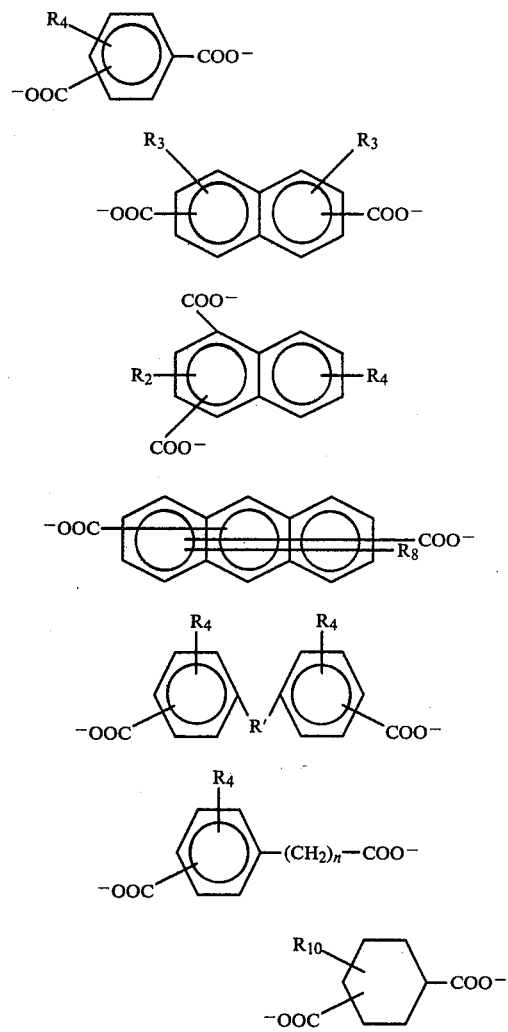

In each of the above formulae, it is preferred that the carboxylates not be on adjacent carbons or in other arrangements (e.g. 1-8-substitution in Formula II) in which there is a tendency for rapid intramolecular anhydride formation as with the formation of phthalic anhydride rather than phthalic acid chloride. It will be appreciated that rings of different sizes and other possible arrangements of carboxylates are possible.

In each of the above formulae, substituents designated R may be H, Cl, Br, F, alkyl, alkoxy, phenyl or any other non-reactive substituent. Preferably R is H in all occurrences. In formula V, the linking substituent R' may be —O—, —S—, —SO$_2$—, alkylene (such as isopropylidene), —CO—, a single bond or any other inert divalent radical. In formula VI n is an integer of 1 to 5.

The alkali or alkaline earth metal which forms a part of the above starting material may be alkali metal, such as lithium, sodium or potassium, and may also be alkaline earth such as magnesium or calcium. In general, the alkali metal salts are preferred, sodium and potassium salts are more preferred and sodium salts are most preferred.

The preferred group of alkali metal or alkaline earth metal salts of aromatic dicarboxylic acids are the disodium and dipotassium salts of terephthalic or isophthalic acids. Most preferred is the disodium salt of terephthalic acid.

These salts are reacted in an inert organic solvent which, because of the limited solubility of the salts, generally takes the form of a slurry. Suitable organic solvents include aromatic hydrocarbons, chlorinated aromatic hydrocarbons and aliphatic chloroalkanes of 1 to 4 carbons, and especially chloromethanes such as dichloromethane.

The term inert is used to mean that the solvent does not interfere with the reaction, nor does it consume any of the reactants. It is not intended, however, that the solvent play no role in the reaction. Furthermore, the term solvent is not meant to require that each reactant, product and by-product dissolve in the solvent. In fact, it is preferred that only the product acid chloride, the reactant phosgene and the tertiary nitrogen compound be soluble to a significant degree in the solvent. It is not critical whether or not the reactant alkali metal or alkaline earth metal salt of an aromatic or cycloaliphatic dicarboxylic acid is soluble to a significant degree in the solvent and, in the examples, this solubility is quite limited. It is preferred that the by-product inorganic salt (e.g. sodium chloride) be insoluble in the solvent for the system.

The amount of solvent present during acid chloride synthesis is not critical, but it is desirable that sufficient solvent be present to dissolve all of the reactant phosgene, tertiary nitrogen compound and product acid chloride. Excesses of solvent beyond this amount are of no advantage. The solvent amount may be similar to or less than the solvent amount in subsequent polymerization.

In general, the amount of phosgene used in the reaction is not critical, but it is desirable that at least about an equal molar amount of phosgene by moles of carboxylate be provided. It is preferred to use at least about a 10% excess, such that phosgene is present at least about 110%, by moles of carboxylate. It will be appreciated that a 10% excess by moles of carboxylate will result in an organic solution with about 5 moles of diacid chloride per mole of unreacted phosgene. If a poly(ester carbonate) is to be produced, then it is more preferred to use from a 20% excess to an amount of phosgene sufficient for both diacid chloride production and formation of carbonate linkages. Thus, if the acid chloride is to be used to produce a poly(ester carbonate) of about equal parts carbonate and aromatic diacid-derived moieties, then about 120% of phosgene by moles of carboxylate to about 150% of phosgene by moles of carboxylate is the more preferred range.

The order of addition of reactants is not critical, but it is preferred that the phosgene be present in the acid chloride synthesis reaction mixture at least as early as the reactant carboxylate salt. Thus, it is preferred to add the carboxylate salt to the solvent already containing the phosgene rather than the reverse. In general, if the carboxylate is added to a solution which contains acid chloride, but which does not contain phosgene, then the somewhat slower reaction between the carboxylate salt and the product acid chloride to form anhydride may occur. When phosgene is present, however, it is believed that the chlorination reaction successfully competes with the anhydride forming reaction with the result that little anhydride is formed.

The reaction is conducted in the presence of a catalytic (i.e. less than stoichiometric by moles of carboxylate) amount of a tertiary nitrogen compound. The requirements for the tertiary nitrogen compound are that it be soluble in the solvent, at least to a limited degree. Tertiary nitrogen compounds having three separate organic substituents may be used. However, it is preferred to use tertiary nitrogen compounds having the nitrogen as part of a heterocyclic ring such as in a quinoline or pyridine nucleus, with compounds having a pyridine nucleus being more preferred. Most preferred is pyridine itself.

While the quantity of tertiary nitrogen compound present is not critical, the advantages of the present invention are best achieved using substantially less tertiary nitrogen compound, by moles, than the moles of carboxylate present. Preferably, the tertiary nitrogen compound, at least in the case of those with the pyridine nucleus, is present in a molar amount of about 0.1 to about 10%, by moles of carboxylate. More preferably, the compound with the pyridine nucleus is present in a molar amount of about 0.2 to about 5%, by moles of carboxylate.

In general, the greater the amount of tertiary nitrogen compound present, the faster the reaction rate. It has been determined, however, that the reaction rate is sufficiently fast, even with the small preferred amounts of tertiary nitrogen compound, to be acceptable. It should be appreciated that, because this reaction produces carbon dioxide as a by-product, in acutal operations the rate may be limited by the ability to withdraw the carbon dioxide and strip it of entrained phosgene and solvent. Thus, even with low amounts of tertiary nitrogen compound present, it may be possible to achieve the maximum reaction rate for the carbon dioxide removal equipment. Since the reaction rate is a function of the particular reactants and tertiary nitrogen compound, the concentration of tertiary nitrogen compound, the particular solvent, the concentration of all ingredients in the solvent and the temperature at which the reaction is conducted, it is difficult to generalize on the reaction rate. Nevertheless, no more than routine experimentation is required to determine the desirable concentrations of the various reactants and tertiary nitrogen compound for a particular reaction in a particular solvent.

Once the acid chloride is synthesized by such process, it is desirable to remove the by-product alkali metal or alkaline earth metal chloride salt before proceeding with polymerization. Since this inorganic salt is generally insoluble in the organic phase, separation may be conducted by centrifugation, filtration or other conventional means. The separation, while desirable, is not required in view of subsequent addition of the aqueous bisphenolate phase in which the inorganic salt would dissolve. It may be desirable, however, to remove the inorganic salt before introducing the aqueous bisphenolate in the inorganic salt concentration may otherwise become excessive during polymerization. Any by-product dicarboxylic acid or anhydride present would also be found preferentially in the solid phase.

Removing the inorganic salt has the additional advantages that the reaction mixture may become easier to stir and easier to separate from a non-miscible phase. Normally other undesirable materials such as by-product anhydride and unreacted carboxylic acid salt are removed with the inorganic salt. If the subsequent reaction is to produce a poly(ester carbonate), then the excess phosgene is normally left in solution and the solvent amount is either left unchanged or increased. If the subsequent reaction is to produce polyester, then any excess phosgene should be removed as by evaporating off, evaporating with it some solvent if the solvent is volatile. Additional solvent may then be added, with the desirable solvent level for either polymerization being that sufficient to keep polymer as formed in solution without excessive viscosities developing that hinder good mixing of phases during reaction or hinder good separation of phases after reaction or hinder handling.

One form of the present invention employs a cycloaliphatic or aromatic dicarboxylic acid chloride in an organic solvent having an amount of tertiary nitrogen compound having a pyridine nucleus between about 0.1 and about 10 percent by moles of carbonyl halide (preferably about 0.2–5 percent) for interfacial reaction with an aqueous bisphenolate solution. While the organic phase is preferably prepared by a process as described above and in copending application Ser. No. 146,942 of Cooke and Van Buskirk, it may also be formed by other means. The interfacial polymerization reaction is conducted by agitating the organic phase with an aqueous bisphenolate phase as described below.

The aqueous bisphenolate phase contains an alkali metal salt or alkaline earth metal salt of a bisphenol such as the sodium salt of bisphenol A. It is permissible, however, to use any bisphenol such as hydroquinone, phenolphthalein and o,o,o',o'-tetramethyldicumylbisphenol as in copending, commonly assigned U.S. Patent applications Ser. Nos. 133,227 (Mar. 24, 1980) of Prevorsek and DeBona and 133,228 (Mar. 24, 1980) of DeBona and Prevorsek.

If some phosgene is left in the organic phase, then poly(ester carbonate) polymers result with, depending on the phosgene to acid chloride ratio, anywhere from about 5 to about 60 parts carbonate residues and from about 40 to about 95 parts diacyl residues for each 100 parts bisphenol residues.

If the phosgene is removed before polymerization, or never present as an excess over that required for acid chloride synthesis, then the product will be a polyester with about equal parts diacyl and bisphenol residues.

During the polymerization, it is desirable that a basic catalyst for polymerization be present together, in the case of poly(ester carbonate) synthesis, with sufficient phosgene to constitute at least 20 percent of the stoichiometric amount for completion of the polymerization reaction. The basic polymerization catalyst may be the tertiary nitrogen compound present from the acid chloride synthesis. It is highly preferred, however, to use a tertiary nitrogen compound with a pyridine nucleus such as pyridine itself, for the acid chloride synthesis, and then use a tertiary nitrogen compound with three separate substituents such as a trialkylamine (e.g. triethylamine) for the polymerization. The same compound, e.g. 4-dimethylaminopyridine, may contain both functionalities. In the preferred case, however, the acid chloride catalyst (e.g. pyridine) is different from the polymerization catalyst (e.g. triethylamine). The phosgene may be carried over from the synthesis of acid chloride, and preferably is so carried over in that excess phosgene increases the yield of acid chloride and eliminates the necessity of adding phosgene during the initial stages of the polymerization. It is desirable that the phosgene be present in an amount somewhat less than that actually required for total polymerization. This permits the avoidance of the formation of polyester blocks and polycarbonate blocks for the reasons described in columns 2 and 3 of U.S. Pat. No. 4,194,038. It is not intended, however, to exclude from the present invention methods in which a high proportion such as 80 or 90 percent of the actually required phosgene (which may be 100% of that theoretically required without consideration of hydrolysis) is present in the organic solution at the beginning of polymerization. It appears that in interfacial polymerizations, unlike the solution polymerizations described in U.S. Pat. No. 4,194,038, excessive haze (in the final polymer) does not occur merely because a large proportion (such as 90 or 100 percent) of the theoretically required phosgene is present with the acid chloride ahead of the bisphenol.

Additional phosgene, if required in a poly(ester carbonate) synthesis, may be added after the polymerization has proceeded to a significant extent; and, preferably, phosgene is added after a substantial period of polymerization in an amount in excess of the stoichiometric amount to assure completion of the formation of the desired carbonate linkages.

As is conventional, other materials may be present during the polymerization, and as particularly phenolic chain regulator and terminator materials such as tert-butylphenol. With routine experimentation, concentrations of such regulators can be determined for a particular combination and concentration of acid chloride and bisphenol to achieve a desired polymer size (as measured by reduced viscosity).

The polymerization reaction conditions are conventional for interfacial production of polyesters and polycarbonates and include sufficient agitation to produce the desired reaction between reactants in different phases. If a reaction results in phases difficult to separate, then greater agitation or other known methods should be tried to achieve clear phase separation. As is conventional, the temperatures and pressures of polymerization are not critical, with approximately atmospheric pressure and room temperature being convenient.

EXAMPLE 1

A 500 ml flask equipped with mechanical stirrer, thermometer, phosgene dip tube, nitrogen inlet and acetone-dry ice condenser attached to a caustic scrubber was charged with 200 ml dichloromethane. The flask was immersed in an ice bath, the temperature was maintained at 2°–4° C. with stirring at approximately 200 rev/min while 31.6 g (319 mmol) phosgene was introduced over 65 minutes. After 0.16 ml (2 mmol) pyridine was added, the temperature of the reaction mixture was raised to 25° C. A stirred slurry of 21.53 g (103 mmol) disodium terephthalate in 60 ml dichloromethane was added over 60 min. A moderate exotherm and steady evolution of carbon dioxide were noted. The reaction mixture was heated to 35° C. and stirred an additional 90 min until the evolution of gas ceased.

The slurry was cooled in an ice bath to 2°–4° C. and filtered under slight nitrogen pressure through a medium sintered glass fritte. The reaction flask and filter-cake were washed with three 70 ml portions of dichloromethane.

The combined solution of about 470 ml containing about 103 mmol terephthaloyl chloride and 114 mmol phosgene was added with a 30 ml dichloromethane solution containing 0.36 g (2.40 mmol) tertbutylphenol to a well stirred aqueous solution of sodium bisphenolate (205 mmol in about 298 ml) and triethylamine (0.65 mmol). The reaction mixture turned yellow momentarily, but after 2–3 minutes became milky. A slight (5°–6° C.) temperature increase was noted.

After 20 min the pH was 2–3 and an aliquot was removed for analysis. 140 ml of aqueous sodium hydroxide (192 mmol) was added to bring the pH back to above 11 and the reactor was swept with phosgene gas until the pH returned to the 5–6 range (5–6 minutes at about 1 g phosgene/min). The mixture increased in viscosity and, after 40 minutes and again after 60 minutes, stirring was momentarily discontinued and the phases separated immediately into a clear aqueous phase and a thick, milky organic phase. Aliquots were taken from the organic phase each time.

The 40 ml of aqueous sodium hydroxide (55 mmol) was added, bringing the pH to above 11, and the mixture was stirred for an additional 30 min. Again the phases separated immediately, and all of the organic layer was taken as the fourth sample.

The first three samples of organic layer were worked up by precipitation in methanol, dissolution in dichloromethane, water extraction until a negative chloride ion test was obtained, filtration, reprecipitation in isopropanol, and vacuum drying (120° C., 1 torr or 133 Pa for 24 h). All separations were quick and sharp with some slight amount of insoluble material present.

The final (fourth) sample was worked up by separating the organic phase from the water phase, diluting it with more dichloromethane, precipitation of the polymer by addition to isopropanol (blender) and washing with isopropanol. The product was then redissolved in dichloromethane and extracted with distilled water until a negative chloride ion test was obtained. It was finally filtered, precipitated by adding to isopropanol, and vacuum dried (120° C., 1 torr or 133 kPa for 24 hr.). Some difficulty was initially encountered with the work-up due to the high viscosity of the final sample but this was overcome by a 4–6 fold dilution with dichloromethane.

Reduced viscosities of the four samples were measured in phenol-tetrachloroethane and were 0.29, 1.61, 1.58 and 1.85 d/g for the four samples. Infrared analysis of the fourth sample showed a 1.94:1 ratio of bisphenol A derived residues to terephtahlate residues. Differential scanning calorimetry (DSC) of the fourth sample indicated a glass transition (Tg) of 192° C.; and thermal gravimetric analysis (TGA) showed major decomposition above 400° C. in a single step, with less than 1% weight loss at 300° C. and 2.5% weight loss at 400° C.

Discs of $\frac{1}{8}$ inch thickness by $1\frac{1}{4}$ inch diameter (3.18 mm by 31.75 mm diameter) molded from the fourth sample at 310° C. exhibited an 18.6 yellowness index, 80.1% transmittance value and 10.9 haze index according to ASTM D-1925 as used in U.S. Pat. No. 4,156,069.

EXAMPLE 2

Example 1 was repeated with the following proportions used in preparation of the terephthaloyl chloride solution:
200 ml dichloromethane 2 mmol pyridine
315 mmol phosgene
105 mmol disodium terephthalate (added over 30 rather than 60 minutes)

After the by-product sodium chloride was filtered out, about 470 ml of solution was reacted as in Example 1. Three aliquots and a fourth, final sample were taken during reaction as in Example 1 and worked up as in Example 1. The reduced viscosities for the four samples were 0.27, 1.40, 1.38 and 1.92 dl/g, the ratio of residues for the fourth sample was 1.92 by infrared, the Tg was 195° C. by DSC and the weight loss by TGA was under 1% at 300° C. and 1.3% at 400° C., with decomposition in a single step above 400° C. Discs molded at 310° C. showed a 13.2 yellowness index, 83.5% transmittance and a 12.0 haze index by ASTM D-1925.

It will be appreciated that lower molecular weights, as for example in the 0.5 to 1.0 dl/g reduced viscosity range, can be obtained by adding more t-butylphenol regulator, with the amount determinable by routine experimentation.

EXAMPLE 3

Example 1 is repeated using, in place of disodium terephthalate, about 100 mmol of the following salts:
(A) dipotassium terephthalate
(B) calcium terephthalate
(C) disodium isophthalate
(D) disodium 4,4'-benzophenonedicarboxylate
(E) disodium 2,6-naphthalenedicarboxylate
(F) disodium 1,4-cyclohexanedicarboxylate The times necessary for relatively complete conversion can be determined by routine experimentation. It can be seen from Examples 14-23 of the copending application of Cooke and Van Buskirk (these Examples being incorporated herein by reference) that the corresponding acid chlorides will be formed. Polymerization is then conducted interfacially to produce the corresponding poly(ester carbonate).

EXAMPLE 4

Example 1 is repeated through the end of carbon dioxide evolution at 35° C. The reaction mixture is then heated to near 40° C. and both phosgene and some dichloromethane are removed by evaporation. The remaining slurry is then filtered as in Example 1 and the filtercake washed as in Example 1, but with sufficient dichloromethane used to bring the combined filtrate solution up to 500 ml.

The resultant 500 ml solution containing about 100 mmol terephthaloyl chloride is reacted interfacially with an aqueous sodium bisphenolate solution (about 100 mmol in about 150 ml) in the presence of about 0.35 mmol triethylamine. Agitation is stopped momentarily every twenty or so minutes and aliquots of organic layer are taken and analyzed for viscosity of the organic phase. Reaction is continued until polymer of the desired molecular weight is formed. If the molecular weight is higher than desired, then the experiment is repeated with various amounts of a regulator such as tert-butylphenol until the desired molecular weight is achieved.

EXAMPLE 5

Example 4 is repeated, using, in place of disodium terephthalate, about 100 mmol of the following salts:
(A) dipotassium terephthalate
(B) calcium terephthalate
(C) disodium isophthalate
(D) disodium terephthalate (50 mmol) and disodium isophathalate (50 mmol)
(E) disodium 4,4'-benzophenonedicarboxylate
(F) disodium 2,6-naphthalenedicarboxylate
(G) disodium 1,4-cyclohexanedicarboxylate Once the acid chlorides are formed as in Examples 14-23 of the copending application of Cooke and Van Buskirk, after reaction times determinable with routine experimentation, then removal of phosgene and of solids, and then polymerization is conducted as in Example 4 to produce the corresponding polyester.

EXAMPLE 6

A solution of 0.05 mol of terephthaloyl chloride (TPC) in 250 ml dichloromethane was filtered through a fine sintered glass funnel, and about 0.055 mol condensed phosgene was added. Pyridine was then added in some runs (0.5 mmol in Runs C and J; 1.5 mmol in Runs D and E; 2.5 mmol in Run F; 3.5 mmol in Run G; 5.0 mmol in Runs H and I) to simulate pyridine carried over from TPC synthesis.

A 146 ml aqueous solution containing sodium hydroxide (0.20 mol), 0.10 mol of bisphenol-A and triethylamine (TEA) (in amounts indicated in Table I) were charged to a three-necked flask equipped with mechanical stirrer operating at a rate of about 575 rev/min. A solution of 0.18 g (1.2 mmol) tert-butylphenol in 15 ml dichloromethane and the above TPC-containing solution were charged simultaneously to the above aqueous bisphenol-A/triethylamine solution. A slight temperature rise (about 5° C.) was observed from room temperature and, in runs with pyridine present, an orange color appeared for about 2-3 minutes. Thereafter the reaction mixture turned milky and increased in viscosity.

After twenty minutes the pH decreased to 3-6. Agitation was stopped momentarily, and the reaction mixture separated into a cloudy aqueous phase and a clear organic phase (containing dissolved polymer with low reduced viscosities in the range of 0.11 to 0.46 dl/g indicative of short oligomers). Stirring was resumed, 0.1 mol of sodium hydroxide was added and phosgene gas was passed over the reaction mixture until the pH decreased back to 7-8 range (aliquots of organic layer being taken in most cases after 20 and 40 additional minutes of total reaction time—other sampling times are indicated in Table I). More aqueous sodium hydroxide (27 mmol) was added to bring the pH up to the 10 to 11 range and the mixture was stirred for an additional 30 minutes.

The various samples of organic layer were precipitated in methanol, filtered, redissolved in dichloromethane and repeatedly washed with distilled water until the wash water tested negatively for chloride ion. The solution was filtered through a sintered glass funnel, precipitated by addition to iospropanol, filtered and vacuum dried at 110° C. and 133 Pa (1 torr).

In addition, with pyridine contents of 3 mole % or less (by moles of diacid chloride) the reaction mixtures separated quickly into two phases, and the subsequent work-up was facilitated, with very little sludge formation. Reduced viscosities of each sample (in phenol-tetrachloroethane) were measured and are reproduced in Table I.

TABLE I

| Run | Pyridine mmol | TEA mmol | Polymerization time (min) | Reduced Viscosity |
|---|---|---|---|---|
| A | 0 | 0.32 | 23 | 0.36 |
|   |   |   | 63 | 0.85 |
|   |   |   | 142* | 0.90 |
| B | 0 | 0.37 | 20 | 0.46 |
|   |   |   | 40 | 1.75 |
|   |   |   | 60 | 1.69 |
|   |   |   | 90 | 1.77 |
| C | 0.5 | 0.32 | 20 | 0.25 |
|   |   |   | 40 | 1.45 |
|   |   |   | 60 | 1.49 |
|   |   |   | 90 | 1.54 |
| D | 1.5 | 0.32 | 21 | 0.19 |
|   |   |   | 60 | 0.60 |
|   |   |   | 120* | 0.58 |
| E | 1.5 | 0.32 | 20 | 0.20 |
|   |   |   | 40 | 0.56 |
|   |   |   | 60 | 0.59 |
|   |   |   | 90 | 0.60 |
| F | 2.5 | 0.32 | 20 | 0.16 |
|   |   |   | 40 | 0.32 |
|   |   |   | 60 | 0.45 |
|   |   |   | 90 | 0.50 |
| G | 3.5 | 0.32 | 20 | 0.16 |
|   |   |   | 40 | 0.31 |
|   |   |   | 60 | 0.31 |
|   |   |   | 90 | 0.43 |
| H | 5.0 | 0.32 | 30 | 0.15 |
|   |   |   | 90 | 0.26 |
|   |   |   | 160 | 0.26 |
| I | 5.0 | 0 | 20 | 0.13 |
|   |   |   | 30 | 0.20 |
|   |   |   | 55 | 0.24 |
| J | 0.5 | 0 | 20 | 0.28 |
|   |   |   | 40 | 0.29 |
|   |   |   | 60 | 0.16 |
|   |   |   | 90 | 0.30 |

*Times greater than 90 minutes in Runs A, D and H resulted from resuming stirring after 60 minutes for varying periods before raising the pH to 11. In each case, base was added after the penultimate sampling, and stirring was resumed for about 30 minutes before the final sample was taken. In some cases, further reaction only lowered the reduced viscosity suggesting that degradation was occurring rather than further polymerization.

The results indicate that low pyridine content in Runs C-E (0.5 to 1.5 mmol or 1–3% by moles of TPC) did not interfere with polymerization to an excessive degree, since reduced viscosities of about 0.50 dl/g were still obtainable. Runs F-H, in which the pyridine content was higher (2.5 to 5.0 mmol or 5–10% by moles of TPC), showed insufficient polymer length or molecular weight being achieved as evidenced by reduced viscosities no greater than 0.50 and generally about 0.4 dl/g or less. It thus appears that, for pyridine, the purchased terephthalic acid chloride and the regulator used in this Example, tolerable levels are up to about 3%, by moles of TPC, with up to about 2% being preferred. These levels correspond to 1.5% and 1.0%, by moles of carbonyl chloride.

It should be appreciated, however, that Example 1 had about 102 mmol terephthaloyl chloride of high reactivity and 2 mmol pyridine (2% by moles of diacid chloride or 1% by moles of carbonyl chloride) and, with comparable regulator levels and reaction conditions, produced polymer of 1.85 dl/g in 90 minutes. This greater value compared to Runs C, D and E of this Example 6 (with 1, 3 and 3% pyridine by moles of diacid chloride) suggests that more pyridine could be tolerated in the polymerization of Example 1 or 2 because of the better acid chloride quality. It is on this basis that the preferred range of about 0.1 to 10% and more preferred range of about 0.2 to 5% of tertiary nitrogen compound with a pyridine nucleus, by moles of carboxylate or carbonyl chloride, have been chosen rather than the lower ranges suggested by Table I.

We claim:

1. A process for the production of a poly(ester carbonate) which comprises:
    (a) reacting an alkali metal or alkaline earth metal salt of an aromatic or cycloaliphatic dicarboxylic acid in an inert organic solvent with phosgene in the presence of at least one tertiary nitrogen compound to form a corresponding aromatic or cycloaliphatic dicarboxylic acid chloride dissolved in the organic solvent, carbon dioxide and an alkali metal or alkaline earth metal chloride salt suspended in the organic solution; and
    (b) mixing the organic solution with an aqueous solution of an alkali metal or alkaline earth metal salt of a bisphenol under sufficient agitation and with sufficient phosgene and tertiary nitrogen polymerization catalyst present to form a poly(ester carbonate) polymer.

2. The process of claim 1 further comprising separating the suspended alkali metal or alkaline earth metal chloride from the organic solution before mixing the organic solution with the aqueous solution.

3. The process of claim 1 or 2 wherein said alkali metal or alkaline earth metal salt of an aromatic or cycloaliphatic dicarboxylic acid is a sodium or potassium salt of isophthalic or terephthalic acid.

4. The process of claim 1 or 2 wherein said alkali metal or alkaline earth metal salt of an aromatic or cycloaliphatic dicarboxylic acid is the sodium salt of terephthalic acid.

5. The process of claim 1 or 2 wherein said at least one tertiary nitrogen compound contains a pyridine nucleus.

6. The process of claim 1 or 2 wherein said at least one tertiary nitrogen compound is pyridine, present in the amount between about 0.1 and about 10%, by moles of carboxylate.

7. The process of claim 6 wherein pyridine is present in an amount between about 0.2 and about 5%, by moles of carboxylate.

8. The process of claim 1 or 2 wherein phosgene is present in said reacting step (a) in an amount at least 10% in excess of the stoichiometric amount of phosgene compared to carboxylate.

9. The process of claim 1 or 2 wherein said alkali metal or alkaline earth metal salt of a bisphenol is a sodium or potassium salt of a bisphenol A.

10. The process of claim 1 or 2 wherein the phosgene present during said mixing step (c) is all introduced in said reacting step (a).

11. A process for interfacially producing a poly(ester carbonate) which comprises:
    (a) mixing an organic solution of an inert organic solvent containing an aromatic or cycloaliphatic dicarboxylic acid halide and a tertiary nitrogen compound containing a pyridine nucleus in an amount between about 0.1 and about 10%, by moles of carbonyl halide, with an aqueous solution of an alkali metal salt of an bisphenol in the presence of a catalytic amount of a tertiary amine polymerization catalyst, with phosgene also being present, to form a poly(ester carbonate) with carbonate moieties and moieties derived from the aromatic or cycloaliphatic dicarboxylic acid halide and from the bisphenol, (b) separating aqueous and organic phases after the poly(ester carbonate) is formed,
(c) washing the organic phase substantially free of halide, and
(d) recovering the poly(ester carbonate) from the washed organic phase.

12. The process of claim 11 wherein the phosgene is substantially all present in the organic solution before mixing.

13. The process of claim 11 wherein the aromatic or cycloaliphatic dicarboxylic acid halide is terephthalic or isophthalic acid chloride.

14. The process of claim 11 wherein the bisphenol is bisphenol A.

15. The process of claim 11 wherein the tertiary nitrogen compound is pyridine present in an amount between about 0.2 and about 5% by moles of carbonyl halide.

16. A process for the production of a polyester which comprises:
(a) reacting an alkali metal or alkaline earth metal salt of an aromatic or cycloaliphatic dicarboxylic acid in an inert organic solvent with phosgene in the presence of at least one tertiary nitrogen compound to form a corresponding aromatic or cycloaliphatic dicarboxylic acid chloride dissolved in the organic solvent, carbon dioxide and an alkali metal or alkaline earth metal chloride salt suspended in the organic solution;
(b) removing any unreacted phosgene from the organic solution; and
(c) mixing the organic solution with an aqueous solution of an alkali metal or alkaline earth metal salt of a bisphenol under sufficient agitation and with sufficient tertiary nitrogen polymerization catalyst present to form a polyester polymer.

17. The process of claim 16 further comprising separating the suspended alkali metal or alkaline earth metal chloride from the organic solution before mixing the organic solution with the aqueous solution.

18. The process of claim 16 or 17 wherein said alkali metal alkaline earth metal salt of an aromatic or cycloaliphatic dicarboxylic acid is a sodium or potassium salt of isophthalic or terephthalic acid, or mixtures thereof.

19. The process of claim 16 or 17 wherein said at least one tertiary nitrogen compound contains a pyridine nucleus.

20. The process of claim 16 or 17 wherein said at least one tertiary nitrogen compound includes pyridine.

* * * * *